United States Patent [19]

Jermyn

[11] 4,444,307
[45] Apr. 24, 1984

[54] DEVICE FOR CLEANING AND STERILIZING A SOFT, PLASTIC LENS

[76] Inventor: Arthur C. Jermyn, 15914 Overview Rd., Poway, Calif. 92064

[21] Appl. No.: 436,505

[22] Filed: Jan. 5, 1983

[51] Int. Cl.³ .................. A45C 11/04; A61L 2/18; B01F 11/00
[52] U.S. Cl. .................. 206/5.1; 366/130; 366/129; 220/82 A
[58] Field of Search .......... 206/5.1; 336/130, 129, 336/237; 220/82 A

[56] References Cited

U.S. PATENT DOCUMENTS

| | | | |
|---|---|---|---|
| 2,208,431 | 7/1940 | Rochow | 366/130 |
| 3,052,158 | 9/1962 | Sonni | 220/82 A |
| 3,052,246 | 9/1962 | Beard | 206/5.1 |
| 3,378,020 | 4/1968 | Grabiel | 206/5.1 |

*Primary Examiner*—William T. Dixson, Jr.

*Attorney, Agent, or Firm*—Lloyd F. Seebach

[57] ABSTRACT

The invention relates to a device for cleaning and sterilizing a soft plastic lens in which the device comprises only three elements; namely, a container for receiving a cleaning or a sterilizing liquid and a lens, a strainer and a cap having a plurality of radially extending impellers. The cap encloses the open end of the container and with movement of the two elements so assembled in a back and forth direction, the cleaning or sterilizing liquid is agitated and swirled with the lens being moved therethrough. The strainer is used as an intermediate member that is enclosed by the cap, when the device is inverted after cleaning, rinsing and sterilizing of the lens, to permit the lens to settle onto the central partition of the strainer before the cap is removed to allow the sterilizing liquid to drain from the container. With removal of the container from the strainer, the lens is retained on the strainer and available for pick-up by a sterile inserter.

3 Claims, 7 Drawing Figures

U.S. Patent  Apr. 24, 1984  4,444,307
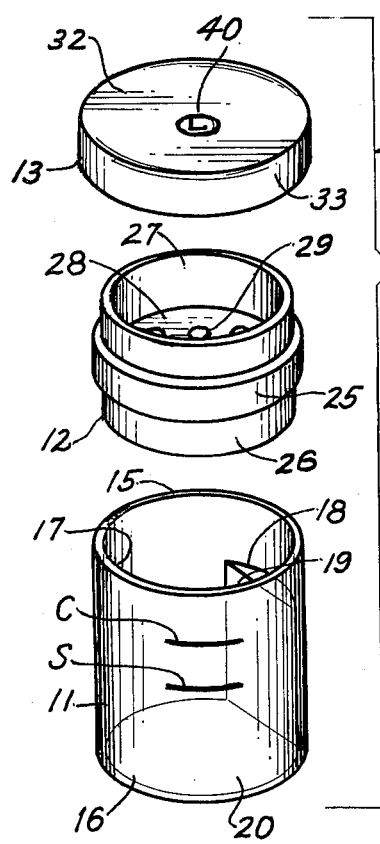
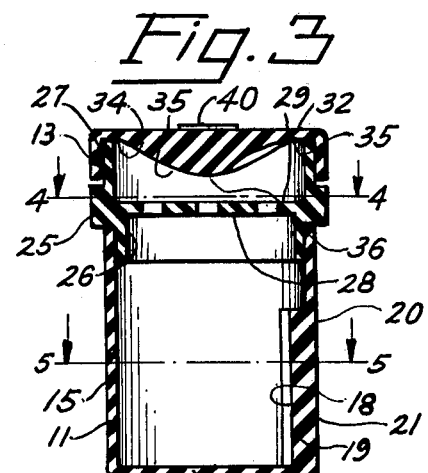
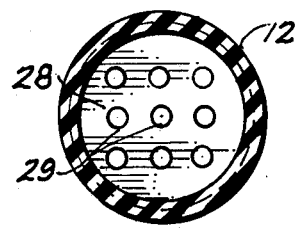
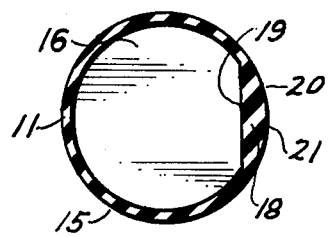
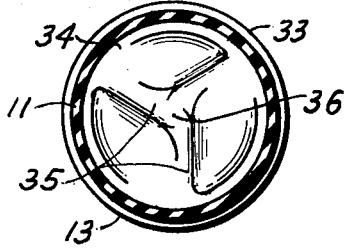
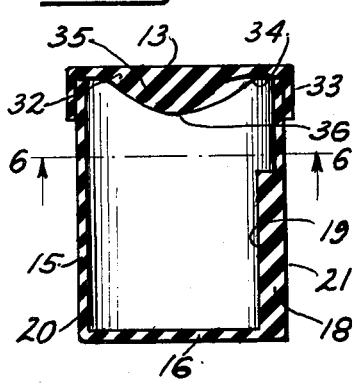
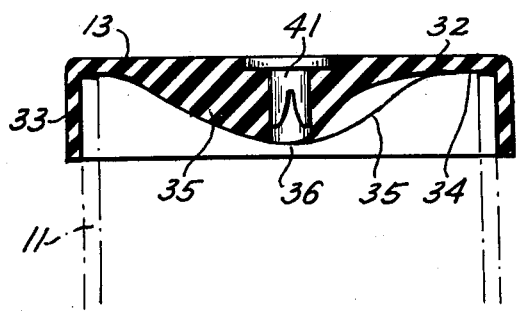

DEVICE FOR CLEANING AND STERILIZING A SOFT, PLASTIC LENS

FIELD OF THE INVENTION

The invention relates to contact lenses and, more particularly, to a device for cleaning and sterilizing a soft, plastic contact lens with a minimum of time and with assurance that the lens will not be damaged in any way.

DESCRIPTION OF THE ART

Heretofore, many devices have been invented and have been advocated for the cleaning of a plastic lens. Most of such devices, however, are primarily for the cleaning of hard plastic contact lenses in that the lens is actually scrubbed in the course of cleaning. Such a device is in no way suitable for cleaning a soft plastic lens. Because of the fragile nature of a soft plastic contact lens, it is generally recommended by the opthamologist or optometrist that the soft lens be cleaned by applying a cleaning liquid to the lens and then moving or rubbing the lens between the fingers. With this method of cleaning, the lens can be damaged by scratching it, by breaking or splitting it or by imbedding dirt and debris that may be on the fingers into the body of the lens. Devices that seek to overcome these difficulties with respect to soft plastic contact lenses are complex and do not provide a very easy way for both cleaning and sterilizing a lens. Further, the prior art does not provide any means or way by which a "chain of sterility" can be maintained from the time the lens is removed from the eye until the lens is again replaced in its position relative to the eye.

SUMMARY OF THE INVENTION

It is an object of the invention to provide a device for cleaning and sterilizing a soft plastic lens in which the lens is merely placed in a container having a lens cleaning liquid that is then agitated and swirled with movement of the container so as to move the lens about in the liquid.

Another object of the invention is to provide a device for cleaning and sterilizing a soft plastic lens in which a container having a lens cleaning or lens sterilizing liquid therein is moved in a back and forth direction whereby impellers forming part of a cap for the container agitate and swirl the liquid.

Yet another object of the invention is to provide a soft plastic lens cleaning and sterilizing device in which a container for receiving a cleaning and sterilizing liquid and the lens is provided with a strainer to permit removal of the liquid while retaining the lens in the container.

Still another object of the invention is to provide a soft plastic contact lens cleaning and sterilizing device in which a container for receiving a cleaning liquid, a sterilizing liquid and the lens is transparent and is provided with a cylindrical lens for producing a magnified image of the lens in the container.

A still further object of the invention is to provide a soft plastic lens cleaning and sterilizing device in which a container for receiving a cleaning liquid, a sterilizing liquid and the lens is provided with means inside the container for alleviating the concentric swirling action of the liquid when agitated so as to enhance the lens cleaning and sterilizing action of the liquid.

And yet another object of the invention is to provide a soft plastic lens cleaning and sterilizing device in which the device comprises an absolute minimum number of parts and is simple in structure and is easy to operate.

The above and other objects and advantages will be apparent to those skilled in the art by the description which follows and which is made in conjunction with the accompanying drawing.

Briefly, The objects of the invention are attained by utilizing a device comprising three simple and distinct parts that can be associated so as to provide a device that is easily operate and very effective. The three basic parts comprise a container, a strainer and an impeller cap. The container for receiving the lens cleaning and sterilizing liquids is, preferably, a cylindrical member made of a transparent material and having an open end. A flat chordal surface extends longitudinally of the container and across the inside of the wall. This surface serves to break up any concentric flow of the liquid when the latter is agitated and swirled. Also, this same surface with the outer surface of the wall of the container forms a cylindrical lens to provide a magnified image of the lens within the container. The strainer is primarily a hollow cylinder with a generally central partition that is perforated with a plurality of holes. One end of the strainer is inserted in the open end of the container and the other end is enclosed by the impeller cap. The impeller cap is used to enclose the open of the container and an open end of the strainer. The inside surface of the cap is provided with a plurality of radially extending impellers for agitating and swirling the liquid in the container. The container is filled to a first index mark on the container with a cleaning liquid and the lens is then removed from the eye and placed in the container. The impeller cap is placed or positioned over the open end of the container. The container, held between the thumb and forefinger, is then moved back and forth, the impeller surfaces on the cap causing the cleaning liquid to be agitated and swirled and the flat surface breaking up any tendency for the liquid to swirl in a strictly concentric pattern. The cap is then removed and the strainer is placed on the container. The cleaning liquid is removed through the strainer while the lens is retained in the container and the sterilizing liquid is poured into the container through the strainer. The cap is then positioned over the open end of the container and the device is again moved to agitate the liquid. The cap is then removed, the sterilizing liquid poured out of the container through the strainer and the container and strainer inverted so the lens now is lying on the partition. At this point the container is seperated from the strainer and a sterile inserter is used to pick up the lens for replacement with respect to the eye. It should be appreciated at this point that the contact lens has been cleaned and sterilized without being touched by the fingers. Also, since the lens is repositioned on the eye by a sterile inserter, there has been no break in the "chain of sterility" from the time the lens is placed in the container until it was replaced in the eye. The device is simple and efficient with a minimum number of parts and accomplishes the cleaning and sterilizing of the lens with great ease.

Other objects and advantages of the invention will be readily apparent to those skilled in the art by the description which follows.

DESCRIPTION OF THE DRAWING

Reference is now made to the accompanying drawing wherein like reference numerals designate like parts and wherein:

FIG. 1 is an exploded perspective view of the associated parts comprising the cleaning and sterilizing device for a soft plastic lens in accordance with the invention;

FIG. 2 is a vertical sectional view through an assembly of the container and the impeller cap in accordance with the invention;

FIG. 3 is a vertical sectional view through an assembly of the container, the strainer and the impeller cap in accordance with the invention;

FIG. 4 is a cross sectional view taken generally along line 4—4 of FIG. 3;

FIG. 5 is a cross sectional view taken generally along line 5—5 of FIG. 3;

FIG. 6 is a cross sectional view taken generally along line 6—6 of FIG. 2; and

FIG. 7 is an enlarged vertical sectional view of the impeller cap showing the variance in pitch of the impeller and one manner of identifying the lens in the container.

DESCRIPTION OF A PREFERRED EMBODIMENT

With reference particularly to FIG. 1, the device, generally designated by the numeral 10, comprises a container 11, a strainer 12 and a cap 13. These three elements or parts comprise a complete device for cleaning and sterilizing a soft plastic lens.

The container 11 is a hollow, cylindrical member comprising a continuous side wall 15, a bottom wall 16 and an open end 17 and is, preferably, made of a transparent material, such as glass or a clear plastic material. As shown in FIG. 1, the container 11 is provided with two index marks C and S which designs the optimum level for the cleaning liquid and for the sterilizing liquid, respectively. The manner in which the two liquids are used will be described in more detail hereinafter. On the inside of the wall 15, a flat chordal section 18 extends longitudinally of the container 11. The chordal section 18 serves two purposes; firstly, the flat surface 19 breaks the tendency for a concentric flow pattern of the liquid when the container is moved as later described and, secondly, the flat surface 19 with the outer curved surface 20 of the wall 15 forms a vertical cylindrical lens or magnifier 21 which produces a magnified image of the lens within the container 11.

The strainer 12 is generally cylindrical in shape and also made of a transparent material, although a translucent or even an opaque material can be used. The strainer 12 is provided with a flange 25 for limiting the extent to which the end 26 can be moved into the open end 17 of the container 11. For this reason, the chordal section 18 cannot extend the full length of the container 11. The opposite end 27 of the strainer 12 receives the cap 13, see FIG. 3. A generally central partition 28 is provided with a pattern of holes 29 for a purpose to be later described.

The cap 13 comprises a flat portion 32 and an extending flange 33 which is capable of engaging the outer surface of the end 27, see FIG. 3, or the outer surface 20 of the container 11, see FIG. 2. The inner flat surface 34 of the cap 13 is provided with a plurality of radially extending impellers 35. As shown in FIG. 6, three such impellers are associated with the cap 13. Obviously, the number of impellers can vary but three has been found to produce satisfactory results. The impellers 35 are molded so as to be a part of the flat portion 32 and extend so as to enter the container 11 or the end 27 of the strainer 12, as seen in FIGS. 2 and 3. The impellers 35 are inclined from a high point 36 generally at the center of the cap 13 to a low point at the surface 34. Also, the impellers vary in pitch on each side of its respective radial line and are similarly oriented. The purpose of the impellers 35 is to agitate and swirl the cleaning and sterilizing liquids when the cap 13 is positioned so as to enclose the open end 17 of the container, as seen in FIG. 2. When the cap encloses the end 27 of the strainer 12, as seen in FIG. 3, the device is inverted to allow the lens to settle onto the partition 28 after which the cap 13 is removed to drain the sterilizing liquid. With subsequent removal of the container 11, the lens is then exposed on the partition for pick-up by a sterile inserter.

As is well known to those skilled in the art, the contact lens in each eye of a wearer is usually of a different prescription and, hence, care must be taken to insure that each lens is repositioned relative to the proper eye. For this reason, the wearer must be certain that the correct lens is replaced with respect to the proper eye. Consequently, the cap 13 can be provided with a releasable decal 40 or a removable pin or button 41, as shown in FIG. 7, each of which would be used to identify the lens being cleaned and sterilized, that is, the lens for the right eye or the lens for the left eye, as noted by an R or an L. Other alternatives would be that two caps be provided, one with an R and the other with an L, or that two devices in accordance with the invention be provided, each of which would be designated for a particular eye. In any event, the wearer must be able to differentiate between the two contact lenses.

The invention will be best understood by a description of the steps involved in the cleaning and sterilizing of a soft plastic lens. For cold sterilization of the lens, the container 11 is filled to the mark C with a liquid comprising distilled water and a suitable cleaning solution. The lens is then removed from the eye and placed in the container 11. The cap 13 is placed over the open end 17 of the container to retain the liquid and the lens. The assembled device, as seen in FIG. 2, is held between the thumb and fingers and moved in a back and forth direction, whereby the liquid is agitated and swirled by the impellers 35 and the lens is moved about within the liquid. The impellers 35 move the liquid in a generally concentric flow pattern which is broken up by the chordal section 18. However, the action is gentle enough so that the lens cannot be damaged should it strike an impeller. Shaking for about 20 seconds will remove all impurities or mucinous deposit from the lens. Cap 13 is then replaced by the strainer 12, the end 26 being inserted into the open end 17 of the container 11. The cleaning liquid is removed through the pattern of holes 29, the lens being retained in the container. Distilled water is poured through the strainer 12 into container 11, the water being agitated by movement of the container so as to rinse the lens. The distilled water rinsing of the lens should be done at least twice as the lens is retained in the container 11 even with removal of the water.

With the lens still in the container 11 and the strainer 12 in position thereon, a saline and sterilizing solution is added through the pattern of holes 29 to the container. The strainer is then replaced by the cap. The device 10 is again moved as described above to agitate and swirl the sterilizing liquid and to move the lens about within the liquid. The cap 13 is removed, after about 20 seconds of movement of the liquid, the strainer replaced in the open end 17 and the cap 13 positioned over the end 27, see FIG. 3. The device, so assembled, is inverted and the lens allowed to settle down and onto the partition 28. This can be easily followed by observing the lens through the magnifier 21. In the event the lens should stick to the wall 15 of the container, the device can be moved to free the lens by agitation of the liquid.

With the lens on the partition 28, the cap 13 is removed and the sterilizing liquid allowed to drain out through the pattern of holes 29. The container 11 is then removed and the clean and sterile lens will be resting on the partition 28. A sterile inserter is used to pick up the lens to reposition it on the proper eye of the wearer. Although the procedure is slightly different, the device 10 can also be used for enzyme cleaning or heat sterilizing when necessary. It should be evident from the foregoing description that the device 10 fulfills a dire need for a simple and easy way to clean and sterilize a soft plastic lens and, at the same time, maintains a "chain of sterility" throughout the full cycle of cleaning and sterilizing.

This invention has been described in detail with particular reference to preferred embodiments thereof, but it will be understood that variations and modifications can be effected within the spirit and scope of the invention.

I claim:

1. A device for cleaning and sterilizing a soft, plastic lens, comprising:
   an elongated, hollow, transparent container having a generally circular bottom wall, a continuous side wall encircling the periphery of the bottom wall and a generally circular open end opposite the bottom wall for selectively receiving a lens cleaning liquid and a lens sterilizing liquid and the lens;
   a strainer having a first generally hollow, cylindrical open end insertable and extending into the open end of the container, a second generally hollow, cylindrical open end extendable beyond the open end of the container and a flat, perforated portion arranged between the first and second open ends of the strainer for receiving the lens on the face of the flat portion facing the first open end of the strainer upon inversion of container to remove the sterilizing liquid and the container from the strainer;
   a removable cap having a generally flat portion, including a first surface and a second surface, and a peripheral flange extending from the portion in the direction of the first surface for selectively enclosing the open end of the container and the second open end of the strainer; and
   a plurality of impellers on the first surface of the removable cap, each of the impellers being similarly oriented and inclined in a radial direction from a high point at the center of the first surface to a low point on the first surface adjacent the flange and each side of which is pitched at a different angle.

2. A device for cleaning and sterilizing a soft, plastic lens in accordance with claim 1 including means formed on the inner surface of the side wall of the container for alleviating a concentric flow of the lens cleaning and sterilizing liquids when the latter are, respectively, agitated and swirled so as to enhance the action of the respective liquid on the lens.

3. A device for cleaning and sterilizing a soft, plastic lens in accordance with claim 2 wherein the alleviating means comprises a flat chordal surface extending from the bottom wall of the container along the inner wall for a portion of the length of the container.

* * * * *